United States Patent
Weaver et al.

[11] Patent Number: 5,348,759
[45] Date of Patent: Sep. 20, 1994

[54] APPARATUS FOR CYANOACRYLATE FINGERPRINT DEVELOPING AND METHOD OF USE THEREFORE

[75] Inventors: David E. Weaver; Everett Clary; Robert Shem; George Taft, all of Anchorage, Ak.

[73] Assignee: State of Alaska, Anchorage, Ak.

[21] Appl. No.: 70,772

[22] Filed: Jun. 3, 1993

[51] Int. Cl.$^5$ .............................................. A61B 5/117
[52] U.S. Cl. .................................... 427/1; 118/31.5; 118/47; 427/145; 427/233; 427/255.6
[58] Field of Search ................ 427/1, 145, 255.6, 223; 118/31.5, 47

[56] References Cited
FOREIGN PATENT DOCUMENTS
0001616  3/1988  World Int. Prop. O. .............. 427/1

Primary Examiner—Janyce Bell
Attorney, Agent, or Firm—Michael J. Tavella

[57] ABSTRACT

A device for developing latent fingerprints is disclosed. The invention has a housing that holds either a pad of steel wool that is impregnated with liquid cyanoacrylate, or a quantity of solid granulated cyanoacrylate. The cyanoacrylate or steel wool is placed around the periphery of the housing. One end of the housing may be tapered to form a connecting tube. This connecting tube is placed on the end of a small propane torch. The torch is used to vaporize the cyanoacrylate in the housing into a vapor, which is then propelled forward from the torch by the velocity of the torch exhaust gases. This vapor is then projected onto the test object, where latent prints will appear within minutes. This invention can be used in any location, including outdoors and does not need a closed environment to work.

5 Claims, 2 Drawing Sheets

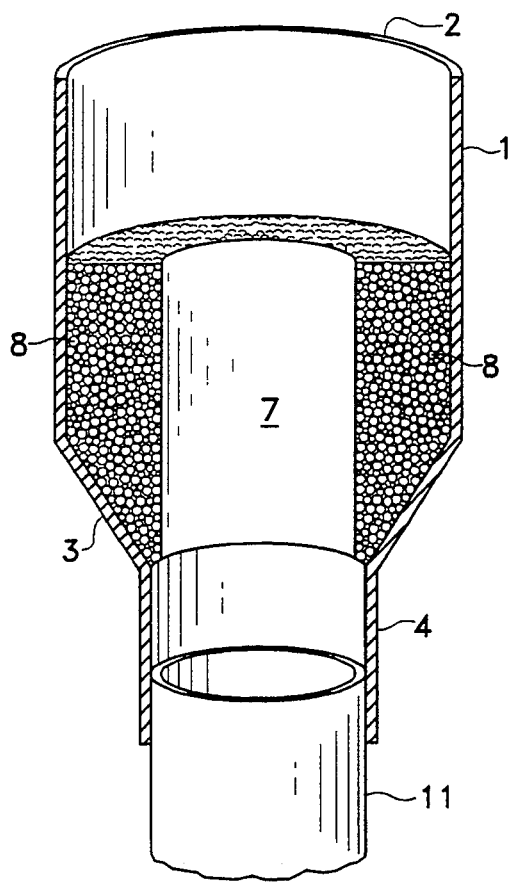
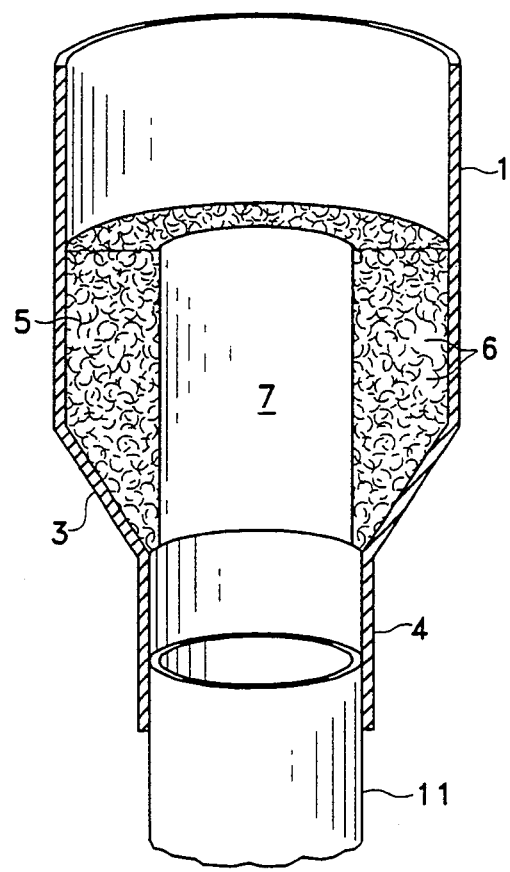
Figure 1    Figure 2
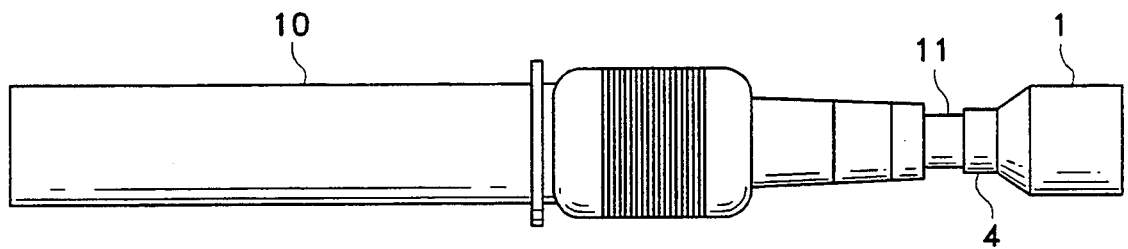
Figure 3

APPARATUS FOR CYANOACRYLATE FINGERPRINT DEVELOPING AND METHOD OF USE THEREFORE

This invention relates to fingerprint developing devices and methods using cyanoacrylate and particularly to fingerprint developing devices and methods using a solid form of cyanoacrylate that is vaporized and then propelled at some velocity toward the object to be tested.

BACKGROUND OF THE INVENTION

It is long known that cyanoacrylate, in vapor form, adheres to fingerprints. Once the vapor cures, the cyanoacrylate forms a white polymer substance that reveals the fingerprint. This technique is known as developing a latent fingerprint. Although this process produces good results, the present technology for developing latent prints involves a time consuming process that must be performed in closed quarters. Current technology uses sheet packets of thick liquid cyanoacrylate. The cyanoacrylate is spread on sheets of material and then sealed. To use, the packet is opened by pulling the two sheets apart which then exposes the cyanoacrylate to the air. Typically, these sheets are placed in a closed vessel such as a large aquarium with the object to be examined. The cyanoacrylate vapors can then adhere to the object, developing any prints that might be on the object. This process can take up to six hours. One system calls for placing several packets throughout a room and then sealing the room for up to 24 hours to develop any prints that may be inside.

Examples of patents that use this technique can be found in U.S. Pat. Nos. 4,550,041, 4,719,119, 4,806,380, 4,260,645, and 4,613,515. As noted above, these devices and methods all suffer from the same drawbacks: they are slow, taking up to several hours to complete the process, and must be used in a closed container.

It is also known that heat accelerates the vaporization of the cyanoacrylate. U.S. Pat. No. 4,719,119 discusses the drawbacks of using heat as it was taught in 1983. Essentially, the heat process uses a laboratory "hot plate" to warm the cyanoacrylate. In use, the opened pouch is placed on the hot plate within a closed container. As the heat is applied, vaporization accelerates. Notwithstanding the safety problems associated with this technique, it still requires that the test be conducted within a closed container, such as an aquarium.

SUMMARY OF THE INVENTION

The present invention overcomes these problems. This invention can be used in any location, including outdoors. The development of the latent prints often takes less than 30 seconds. The invention has a housing that holds a quantity of solid granulated cyanoacrylate. The cyanoacrylate is placed around the periphery of the housing. One end of the housing is tapered to form a connecting tube. This connecting tube is placed on the end of a small propane torch. The torch is used to vaporize the cyanoacrylate in the housing into a vapor, which is then propelled forward from the torch by the velocity of the torch exhaust gases. This vapor is then projected onto the test object, where latent prints will appear within seconds.

An alternative design uses an empty housing that is packed with steel wool. The steel wool is then impregnated with liquid cyanoacrylate, which is then allowed to dry. The device is operated as before only after the cyanoacrylate has been completely vaporized, the steel wool remains. Thus, the housing can be reload with fresh liquid cyanoacrylate for the next test.

BRIEF DESCRIPTION OF THE DRAWINGS

FIG. 1 is a cross-sectional view of the housing with a load of cyanoacrylate ready for use.

FIG. 2 is a cross-sectional view of the housing loaded with steel wool impregnated with cyanoacrylate, ready for use.

FIG. 3 is a side view of the housing as placed on the small torch.

DETAILED DESCRIPTION OF THE INVENTION

Figure 4:
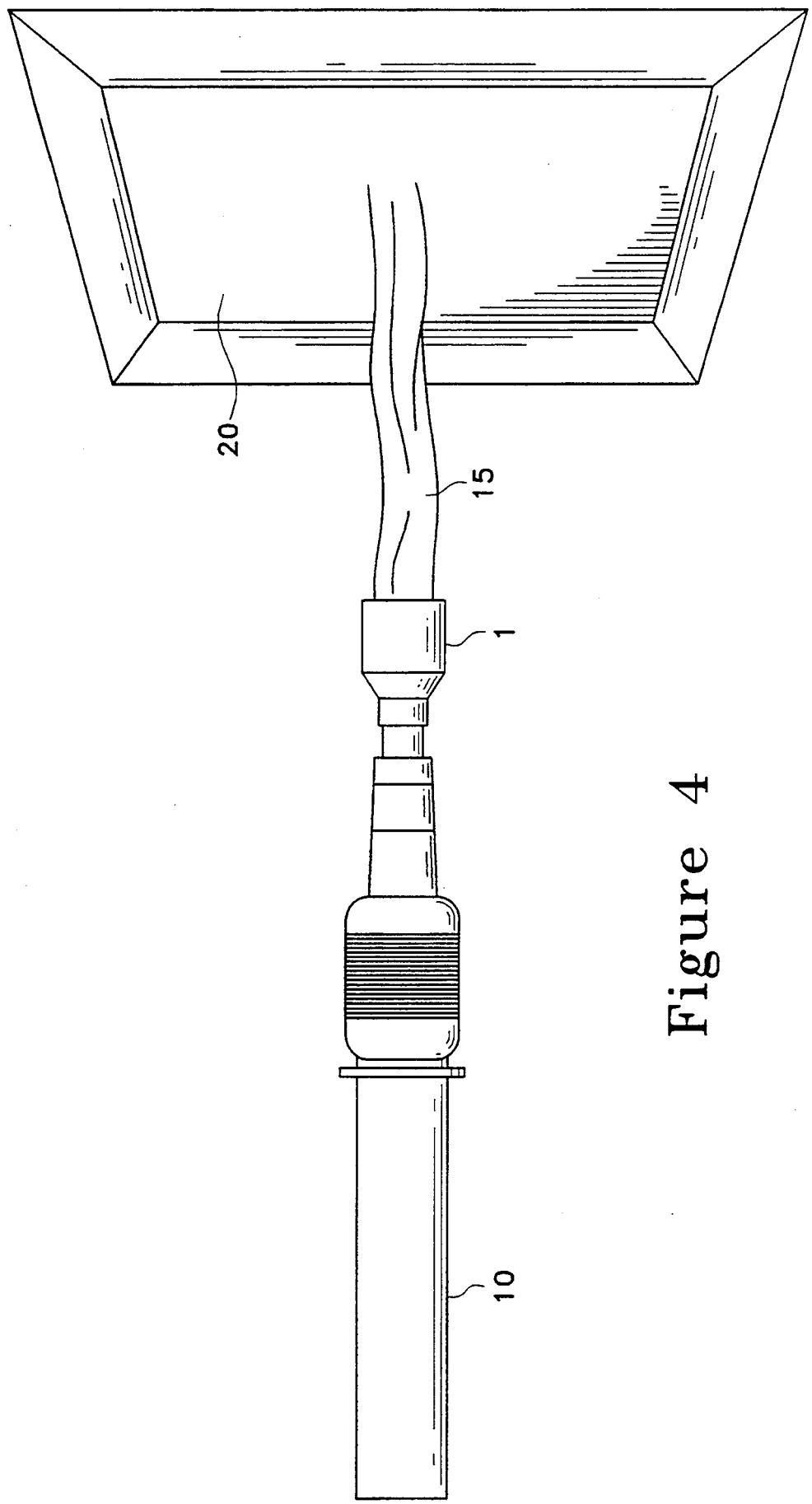
FIG. 4 is a detail view of the device in use.

Referring now to the drawings, the device has a cylindrical housing 1. The housing is open at the top 2. The bottom of the housing 3 can be tapered as shown. In the preferred embodiment, the taper is used. This allows the housing 1 to be placed onto the exhaust port of a small commercially available propane torch, as discussed below. A connecting tube 4 is attached to the tapered base 3. This assembly can be constructed from one piece of metal.

In the preferred embodiment, the entire housing 1 is hollow. This permits a quantity of steel wool 5 to be packed to be packed within the housing. Liquid cyanoacrylate 6 is poured over the steel wool 5. When the steel wool has been properly packed, a cylindrical opening 7 is then formed. This opening conforms to the diameter of the torch ejector 11 (see FIGS. 2 and 3). Typically, the housing can be sized to match different sized torches.

In the preferred embodiment, a small propane torch 10, as shown in FIG. 3, is used to vaporize the cyanoacrylate 6 stored within the housing. The preferred torch is a ULTRATORCH model UT-50. These torches are available from the Master Appliance Corporation, 2420 18th Street, Racine, Wis. 53401. These torches provide sufficient heat to vaporize the cyanoacrylate. This size torch can be used indoors or outdoors.

In use, the torch 10 is lit. Then the housing 1 is placed over the lit torch ejector 11 at the connecting tube 4. The exhaust is then directed toward the object to be tested. FIG. 4 shows the device in use. As the cyanoacrylate 6 is vaporized, it is propelled forward toward the object being tested 20. This forward motion of the exhaust gas, 15 focuses the cyanoacrylate stream on the object and produces much faster developing times. This compares to the evaporative type developers, discussed above, that must operate in a closed environment and over long periods of time.

When the cyanoacrylate 6 is used up, the steel wool 5 can be again impregnated with fresh cyanoacrylate for the next use.

An alternative embodiment used granulated, cured cyanoacrylate 8 that is packed around the housing. When the granulated cyanoacrylate 8 is used up, the housing 1 can be discarded and a new housing can be substituted and the process can continue. It is possible to change housings by using pliers without shutting off the torch, although this is not recommended.

The present disclosure should not be construed in any limited sense other than limited by the scope of the claims having regard to the teachings herein and the prior art being apparent with the preferred form of the invention disclosed herein that reveals details of structure of a preferred form necessary for a better understanding of the invention and may be subject to change by skilled persons within the scope of the invention without departing from the concept thereof.

I claim:

1. A device for developing latent fingerprints on objects using cured cyanoacrylate comprising:
   a) a cylindrical housing having an open top and an open bottom and a solid wall, said cylindrical housing also having a quantity of granulated, cured cyanoacrylate packed against said wall such that said cyanoacrylate forms a cylinder within the cylindrical housing having an open area in its center;
   b) heating means having sufficient temperature to sublimate the cured cyanoacrylate, said heating means also producing an exhaust gas having a forward velocity that projects the sublimated cyanoacrylate from said housing in an outward direction; and
   c) means to removably attach said heating means to the bottom of said housing such that said exhaust gases pass through said housing and exit therefrom through said top of said housing.

2. The device for developing latent fingerprints of claim 1 wherein the cured cyanoacrylate comprises granulated pellets that are compressed into a solid form.

3. The device for developing latent fingerprints of claim 1 wherein the cured cyanoacrylate comprises a solid, cylindrical block of material having an open center.

4. The device for developing latent fingerprints of claim 1 wherein said heating means comprises a portable blowtorch.

5. The method of developing latent fingerprints on an object, using cured cyanoacrylate, comprising the steps of:
   a) attaching a housing containing a cured, granulated form of cyanoacrylate to the exhaust port of a propane torch;
   b) lighting said torch, thereby producing a relatively high temperature exhaust gas, having a forward velocity, that is projected from said exhaust port;
   through said cyanoacrylate in said housing attached to said exhaust port, causing said cyanoacrylate to sublimate into a vapor;
   d) having said exhaust gas project said cyanoacrylate vapor in a forward direction onto said object for testing.

* * * * *